(12) United States Patent
Moore, III et al.

(10) Patent No.: US 6,402,757 B1
(45) Date of Patent: Jun. 11, 2002

(54) CANNULATED FASTENER SYSTEM FOR REPAIR OF BONE FRACTURE

(75) Inventors: Robert J. Moore, III, Houston, TX (US); Mark V. Vandewalle, Pierceton, IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 09/523,821

(22) Filed: Mar. 13, 2000

Related U.S. Application Data

(60) Provisional application No. 60/123,914, filed on Mar. 12, 1999.

(51) Int. Cl.[7] ............................................. A61B 17/00
(52) U.S. Cl. .......................... 606/80; 606/86; 606/72; 606/73; 606/104
(58) Field of Search ............................. 606/80, 53, 67, 606/64, 86, 104, 102, 72, 73, 61; 411/399

(56) References Cited

U.S. PATENT DOCUMENTS

| | | | | |
|---|---|---|---|---|
| 298,427 A | * | 5/1884 | Stone | ............................ 411/387 |
| 466,463 A | | 1/1892 | Holland | |
| 1,894,708 A | | 1/1933 | Sardeson | |
| 3,903,784 A | | 9/1975 | Dekker | |
| 4,450,834 A | * | 5/1984 | Fischer | ............................ 606/80 |
| 4,572,720 A | | 2/1986 | Rockenfeller et al. | |
| 4,697,969 A | | 10/1987 | Sparkes | |
| 5,203,657 A | | 4/1993 | Nagoshi et al. | |
| 5,249,882 A | | 10/1993 | Nagoshi et al. | |
| 5,374,270 A | * | 12/1994 | McGuire et al. | ............... 606/86 |
| 5,470,334 A | * | 11/1995 | Ross et al. | ...................... 606/72 |
| 5,516,248 A | * | 5/1996 | DeHaitre | ...................... 411/399 |
| 5,683,217 A | | 11/1997 | Walther et al. | |
| 5,997,541 A | * | 12/1999 | Schenk | ......................... 606/73 |
| 6,042,314 A | * | 3/2000 | Guelck | ......................... 411/399 |
| 6,197,031 B1 | * | 3/2001 | Barrette et al. | ................ 606/80 |

* cited by examiner

*Primary Examiner*—Pedro Philogene
(74) *Attorney, Agent, or Firm*—Harness, Dickey & Pierce, P.L.C.

(57) ABSTRACT

A fastener assembly for repairing fractured bone material includes a wire having a wire leading end for forming a bore through the bone material and a wire trailing end for extending beyond a near-side cortex of the bone material. The fastener includes a head portion having spaced-apart grooves defining cutting edges, a lower portion having threads, and an axial aperture therethrough for receiving the wire. The fastener is adapted to slide axially over the wire trailing end and be driven toward the wire leading end to countersink in the bone material. A driver including a driver body having an axially disposed aperture therethrough for accommodating said guide wire, and a driver head having fingers adapted to engage the spaced-apart grooves of the fastener head portion, is adapted to drive the fastener in the bone material. A measuring sleeve including a tubular body adapted to be positioned generally coaxially relative the wire trailing end and abutting the bone material includes a graduated scale thereon for comparison to the wire trailing end, whereby the depth of the bore can be determined.

38 Claims, 7 Drawing Sheets

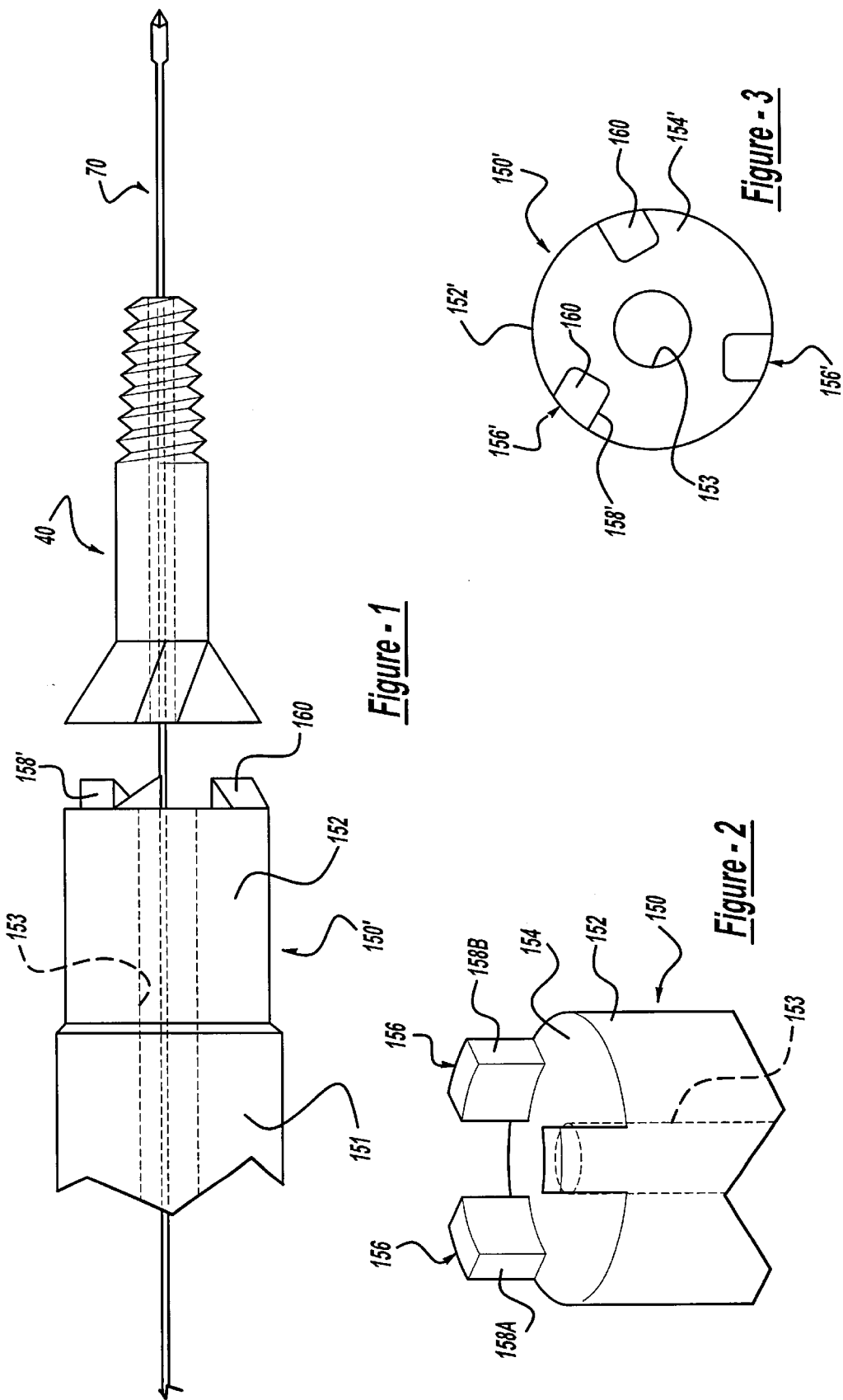

CANNULATED FASTENER SYSTEM FOR REPAIR OF BONE FRACTURE

CLAIM FOR PRIORITY

This patent application claims priority to U.S. Provisional Patent Application No. 60/123,914, filed Mar. 12, 1999.

FIELD OF THE INVENTION

The present invention relates to a fastener system for repairing a bone fracture and, more particularly, a driver, a measuring device, and a self-drilling, self-tapping, self-counter-sinking, cannulated fastener for use with a guide wire to repair a bone fracture.

BACKGROUND OF THE INVENTION

While forming a countersunk recess is known in the surgical arts, such recesses are conventionally formed using a separate step and tool. The use of self-countersinking bolts, threaded fasteners, or screws is known in the carpentry and metalworking arts, but such designs are not readily acceptable for use in bone repair. For example, U.S. Pat. No. 5,683,217 to Walther et al. teaches a self-counter-sinking screw wherein the head of the threaded screw has an underside including triangular recesses with edges for cutting or burring a conical countersink in a workpiece. The recesses accommodate material removed by the countersinking. Further, such conventional fasteners are inefficiently driven by applying torque near the rotation axis. A fastener having an improved structure at a reasonable cost, that can form a countersunk recess in a bone to be repaired, that is adapted for use with a guide wire, and that can be efficiently driven by applying torque at its periphery, is needed. Further, there is a need for a measuring device for determining the depth of a fractured bone to be repaired so that an appropriately sized fastener can be selected to repair the fracture.

SUMMARY OF THE INVENTION

A fastener assembly for repairing a bone fracture including a cannulated fastener, guide wire, measuring sleeve, and driver maximizes simplicity and cost effectiveness. The fastener provides an improved structure at a reasonable cost for self-tapping, self-drilling, and self-countersinking in a bone to be repaired. Further, the guide wire eases insertion of the fastener and, with the measuring device, simplifies measurement of a bore in bone material, whereby the depth of a fractured bone to be repaired can be easily determined so that an appropriately sized fastener can be selected to repair the fracture. The driver efficiently drives the fastener by applying torque at the periphery of the fastener head.

More particularly, a fastener assembly according to the invention includes a wire having a wire leading end for forming a bore through the bone material and a wire trailing end for extending beyond a near-side cortex of the bone material. The fastener includes a head portion having spaced-apart grooves defining cutting edges, a lower portion having threads, and an axial aperture therethrough for receiving the wire. The fastener is adapted to slide axially over the wire trailing end and be driven toward the wire leading end to countersink in the bone material. A driver including a driver body having an axially disposed aperture therethrough for accommodating the guide wire, and a driver head having fingers adapted to engage the spaced-apart grooves of the fastener head portion, is adapted to drive the fastener in the bone material. A measuring sleeve including a tubular body adapted to be positioned generally coaxially relative the wire trailing end and abutting the bone material includes a graduated scale thereon for comparison to the wire trailing end, whereby the depth of the bore can be determined.

BRIEF DESCRIPTION OF THE DRAWINGS

FIG. 1 is a partial side view of a driver, fastener, and guide wire according to the invention;

FIG. 2 is a partial perspective view of a head for a driver according to the invention;

FIG. 3 is a top view of another embodiment of a head for a driver according to the invention;

DETAILED DESCRIPTION OF THE PREFERRED EMBODIMENTS

Figures 4, 5:
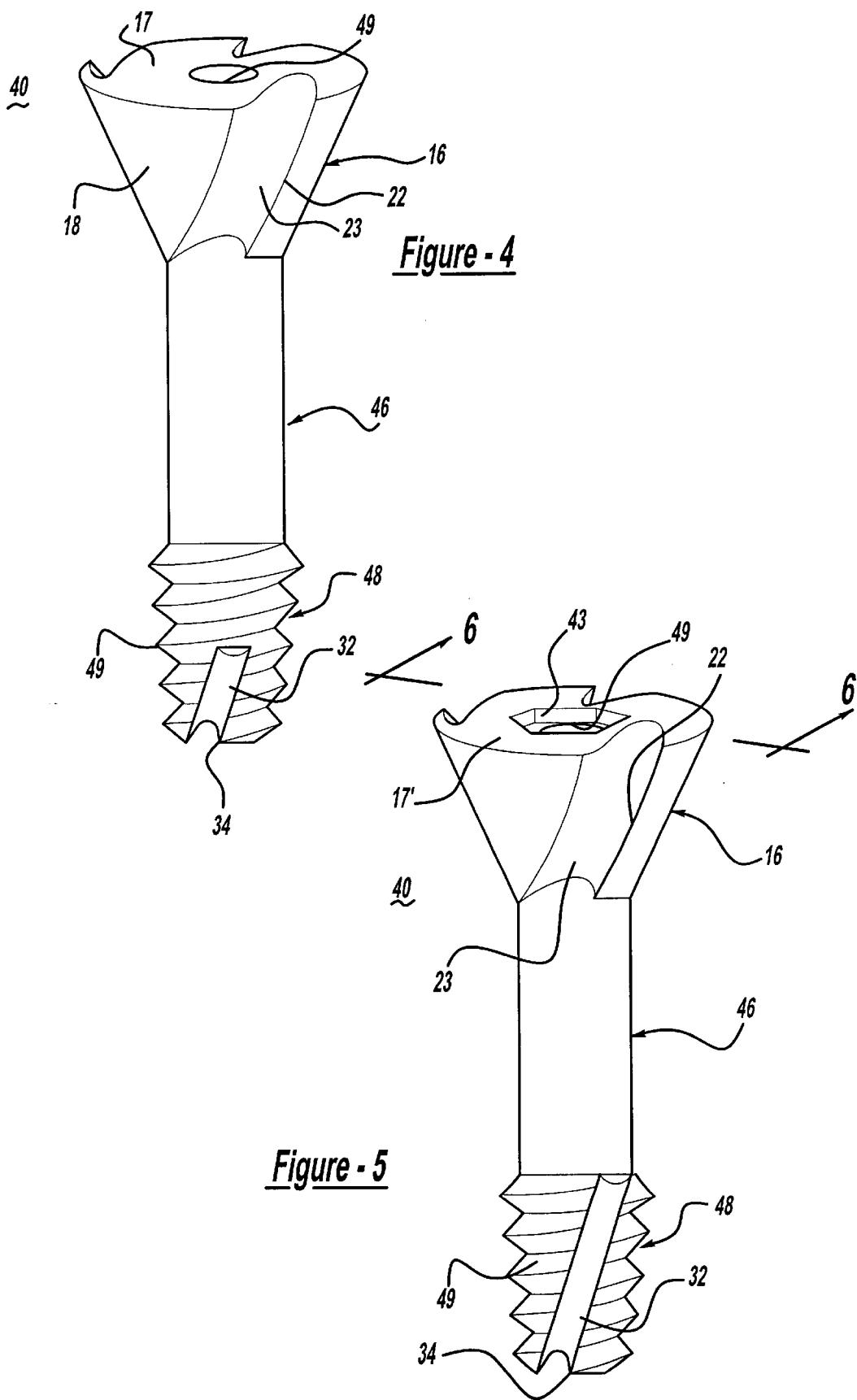
FIG. 4 is a perspective view of a fastener according to the invention.
FIG. 5 is a perspective view of an alternative embodiment of a fastener according to the invention.

The fastener system according to the invention includes a novel driver, guide wire, measuring device, and fastener for repairing a bone fracture. With reference to the drawings, a driver 150 according to the invention is particularly adapted to drive a threaded fastener 40 according to the invention. A fastener assembly according to the invention includes the threaded fastener 40, a guide wire 70, and a measuring device. Preferably the measuring device is a measuring sleeve 100, but can alternatively be a ruler 90. More particularly, the threaded fastener 40 is adapted for use in repairing fractured bone material 80, which has a near side bone cortex 81 and a far side bone cortex 82. When driven into the bone material 80, the wire 70 guides the threaded fastener 40. Preferably, the threaded fastener 40 is driven by the driver 150, but can alternatively be driven by conventional driver, such as a phillips or slot screwdriver or a socket-type driver.

Figure 6:
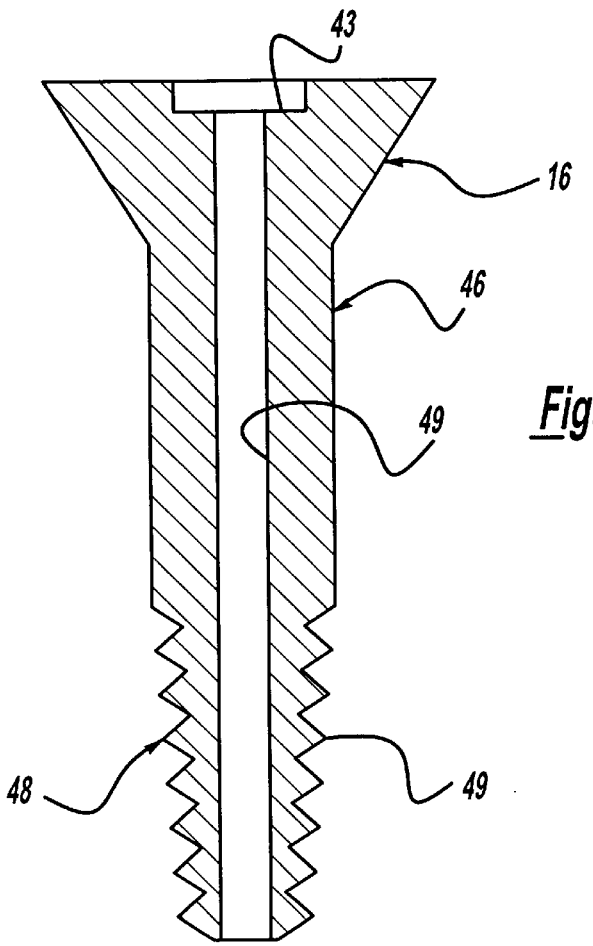
FIG. 6 is a side sectional view of the fastener along line 6—6 of FIG. 5.

The threaded fastener 40 according to the present invention, as best shown in FIGS. 4–6, includes a head portion 16, a shank portion 46, and a threaded end portion 48. The head portion 16 has a flat top surface 17 and a rounded outer peripheral region 18. The outer peripheral region 18 slopes from the flat top surface 17 to the shank portion 46 at approximately 45 degrees, and is preferably in a range of 35 to 65 degrees. In an alternative embodinent shown in FIG. 5, a flat top surface 17' includes a hexagonal recess 43, which is adapted to receive, for example, a hexagonally shaped head of a conventional socket-type driver for applying torque to the threaded fastener 40 during insertion thereof into the bone material 80, and for removal of the threaded fastener 40 from the bone material 80. Other types of recesses or tool gripping portions can be used instead of the hexagonal recess 43, and such variations are contemplated as being within the scope of the present invention.

The head portion 16 further includes a plurality of cutting edges 22 for countersinking the threaded fastener into the near side bone cortex 81 during insertion. The cutting edges 22 are preferably trailing edges of angularly disposed, equi-angularly-spaced arcuate grooves 23. The cutting edges 22 are formed by cutting, grinding, or pressing the head portion 16 to form the grooves 23, which terminate in the cutting edges 22. The cutting edges 22 are preferably angled between 15 and 30 degrees relative the longitudinal axis of the fastener 40 to form an aggressive cutting angle. The angle of the cutting edges 22 and the outer peripheral region 18 can vary depending upon the particular application. The cutting edges 22 burr the bone material 80 to countersink the fastener 40 in the bone material 80 to form a nearly flush surface between the head portion 16 and the near side bone cortex 81. The grooves 23 accommodate burred bone material during insertion of the fastener 40 into the bone material 80. Preferably, three cutting edges 22 are provided, with more or fewer cutting edges 22 being provided depending on the application. By countersinking, the threaded fastener 40 is protected from accidental bumping or striking, which tends to weaken a repaired bone. Further, countersinking minimizes soft tissue irritation from the fastener head portion 16 and protects vital structures in the body that may lie in close approximation to the fastener head 16.

The threaded end portion 48 includes threads 49 and at least two cutting edges 32, which are preferably equi-angularly spaced. The threads 49 of the threaded portion 48 are preferably self-tapping. The cutting edges 32 are preferably fluted, which permits avoiding the necessity of a separate drilling step. Preferably, the cutting edges 32 are generally straight grooves formed in opposite sides of the threaded portion 48. As a result of the shape of the cutting edges 32, the tip portion 34 has a very sharp cutting edge, which assists self-tapping. As shown in FIG. 4, the cutting edges 32 are disposed at the lower end of the threaded end portion 48. In an alternative embodiment, as shown in FIG. 5, the cutting edges 32 extend from the lower end to the upper end of the threaded end portion 48, whereby the cutting edges 32 are able to self-cut during insertion as well as removal of the fastener 40. While shown to be continuous in FIG. 5, the cutting edges 32 may alternatively be discontinuous.

With reference to FIG. 6, a through-passage 49 extends axially through the head portion 16, the shank portion 46, and the threaded end portion 48 of the fastener 40. The through-passage 49 is sized to accommodate passage of the guide wire 70 while inserting the fastener 40. According to the preferred embodiment, the through-passage 49 has a diameter of approximately 0.062 inches for a guide wire 70 having 0.050-inch diameter body. The diameters of the through-passage 49 and the guide wire 70 are variable depending on the particular application, but should be complimentary.

Figure 7:
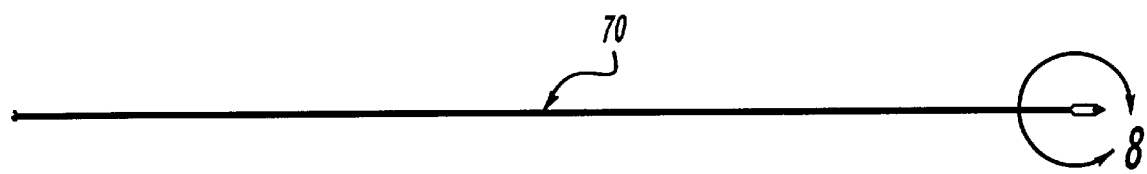
FIG. 7 is a side view of the guide wire of FIG. 1.
Figure 8:
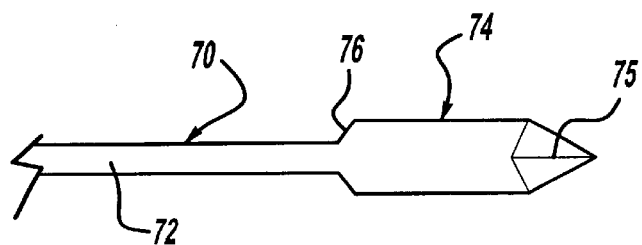
FIG. 8 is an enlarged side view of a cutting tip of the guide wire of FIG. 7.

As best shown in FIGS. 7 and 8, the guide wire 70 includes an elongated cylindrical body 72 and a tip 74 that is slightly enlarged relative the body 72. A neck 76 separates the body 72 and tip 74. The body 72 is preferably substantially longer than the axial length of the threaded fastener 40. Particularly, the length of the guide wire 70 should be long enough to guide the wire 70, yet short enough to avoid injuring vital structures that may lie at the border of the far side bone cortex 82. The guide wire 70, which guides the threaded fastener 40 during insertion into the bone material 80, may be relatively rigid or flexible, but is preferably sufficiently strong and resilient that it does not break off when inserted into the threaded fastener 40. Further, the guide wire 70 is adapted for use with a measuring device to determine whether the threaded fastener 40 is at the desired depth in the bone material 80, or for measuring the insertion depth of the threaded fastener 40 into the bone material 80.

The tip 74 of the guide wire 70 is preferably shaped to cut bone material 80, and is shown to have a generally arrow-head shape. Alternatively, the tip 74 may be blunt or rounded. Where a blunt tip is used, a separate drilling step may be necessary in order to insert the guide wire 70 into the bone material 80. The tip 74 preferably includes cutting edges 75, which facilitate insertion of the guide wire 70 into the bone material 80. Preferably, the tip 74 has a length of approximately three to four millimeters, and a width of approximately 0.060 inches. The lengths and widths are variable depending on the particular application.

The neck portion 76 of the guide wire 70 should have a slightly tapered contour for strength, thereby reducing the risk of breaking off the tip 40 in the surgical site. The greater the difference between the diameter of the tip 74 and the guide wire 70, the more precise the measurement of the length of the bore through the bone material 80. This feature further avoids the tip 74 being retracted into the bone material 80 through the far side bone cortex 82 when the guide wire 70 is drawn towards the near side cortex 81 for measuring the depth of the bone to be repaired.

As shown in FIGS. 1 through 3, the driver 150 according to the invention is particularly adapted to drive a fastener by applying torque at a peripheral edge of the fastener head. For example, the driver 150 is particularly useful to drive the fastener 40 according to the invention, but can be used to drive any fastener with grooves or passages disposed along the periphery of the fastener head. More specifically, the threaded fastener 40 as shown in FIG. 4, which does not include a central hexagonal recess 43, or any other conventional phillips or slot recess, can be driven by the driver 150.

The driver 150 includes a body 151 and drive head 152, which has a generally planar end surface 154 with generally perpendicularly extending prongs 156. A through-passage 153 extends axially through the body 151 and drive head 152 to accommodate the guide wire 70 during insertion of the fastener 40. The prongs 156 are particularly adapted to engage the arcuate grooves 23 of the fastener 40 to drivingly insert or remove the fastener 40 by applying torque along the periphery of the head 16. Accordingly, as many prongs 156 are provided as grooves 23 in the fastener 40, whereby the driver 150 is complimentary to the fastener 40. As shown in FIG. 2, the prongs 156 are generally block-like extensions having a rectangular cross-section, and include sides 158A and 158B, which are adapted to drivingly engage the arcuate walls of the groove 23 to rotate the fastener 40. More specifically, depending on the direction of rotation of the fastener 40, either the wall 158A or the wall 158B engages a surface of the arcuate groove 23. In this manner, the driver 150 is able to insert or remove the fastener 40.

An alternative embodiment of the driver is shown in FIG. 3 as a driver 150', and includes a generally planar surface 154' from which prongs 156' extend generally perpendicularly. The prongs 156' are generally block-like extensions having a triangular cross-section, and include a wall 158' disposed generally perpendicular to the surface 154' and a relief wall 160 angularly extending from the surface 154' to a distal end the wall 158'. The relief wall 160 provides a flow path for burred bone material to exit the arcuate groove 23 during insertion of the fastener 40. Because of the relief walls 160, however, the driver 150' is not able to remove the fastener 40; i.e., the walls 158' only allow the driver 150' to rotate the fastener 40 in the insertion direction, allowing the relief walls 160 to accommodate the flow of burred bone material. Accordingly, a driver similar to driver 150 is necessary for removal of the fastener 40.

Figure 9:
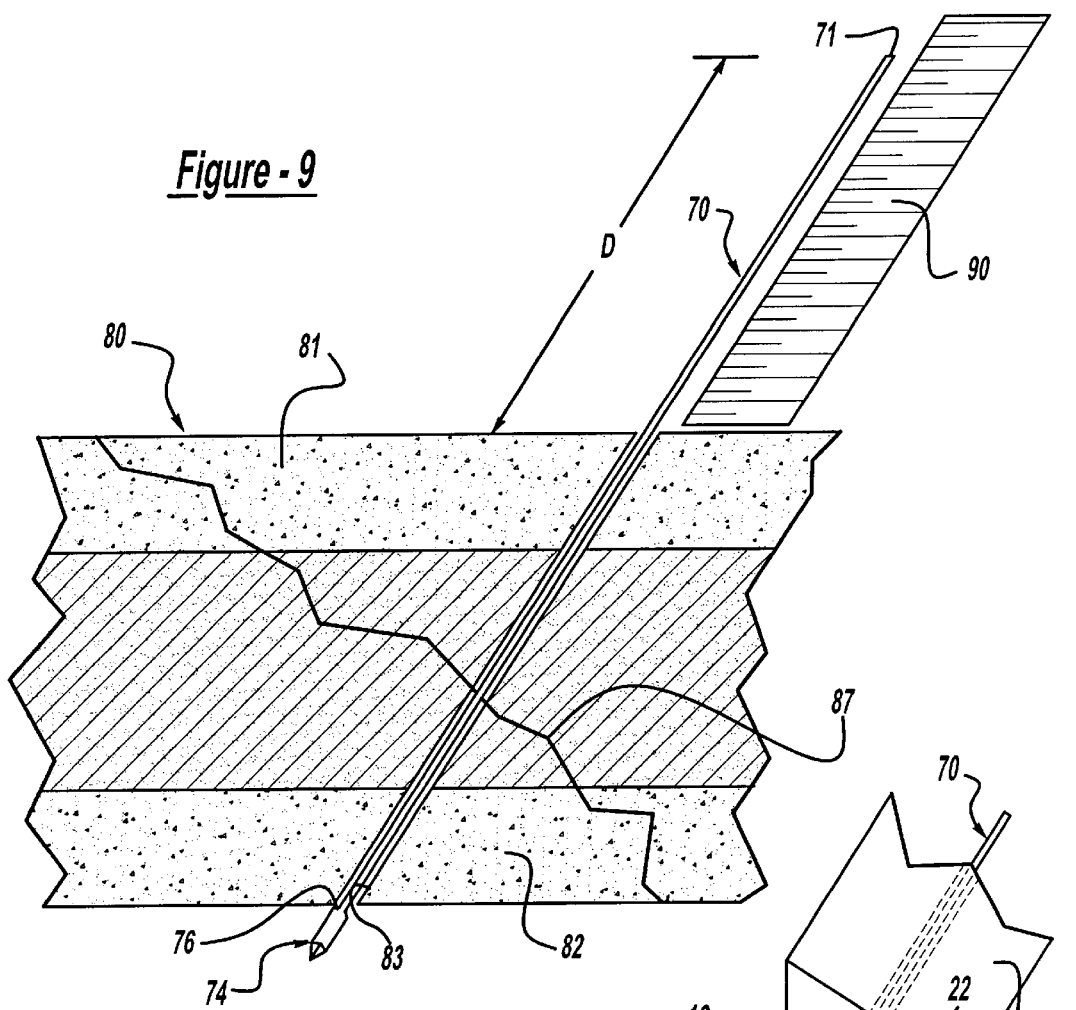
FIG. 9 is a partial sectional view of the guide wire in the bone material with a measuring device according to the invention.

In use, as illustrated in FIG. 9, the guide wire 70 is driven into the bone material 80 using a tool (not shown) to rotate the guide wire 70 such that the tip 74 forms a bore 83 through the near side bone cortex 81, the bone material 80, and the far side bone cortex 82. Preferably, the cutting tip 74 includes a sharpened tip 75 capable of cutting or boring through the bone material 80, thereby avoiding the step of drilling through the bone material 80 prior to insertion of the guide wire 70. The guide wire 70 is able to slide axially in the bore 83, encountering resistance during removal when the tip 74 attempts to re-enter the far side bone cortex 82. More specifically, as the guide wire 70 is being moved in the direction opposite of the insertion direction, the neck portion 76 of the guide wire 70 contacts the far side bone cortex 82. This encountered resistance during removal serves as a useful indicator of the location of the far side bone cortex 82.

A measurement can be made of the bone depth by measuring the portion of the known-length guide wire 70, from an end 71 thereof, using a ruler 90 or other similar measuring device. More specifically, the end 71 of the guide wire 70 extends from the near side bone cortex 81 of the bone material 80 by a distance D, which when compared with the known total length of the guide wire 70, it is possible by simple subtraction to obtain the thickness of the bone to be repaired. With this information, a proper size threaded fastener 40 can be selected, which eliminates the need for a depth gage or separate measuring device in the screw set. Further, an x-ray may be taken while the guide wire 70 is inserted, or after the threaded fastener 40 is inserted, especially in circumstances where the guide wire 70 does not exit the far side bone cortex 82 and the threaded fastener 40 is purposefully fixed without exiting the far side cortex; i.e., the threads remain within the cancellous bone.

Figure 10:
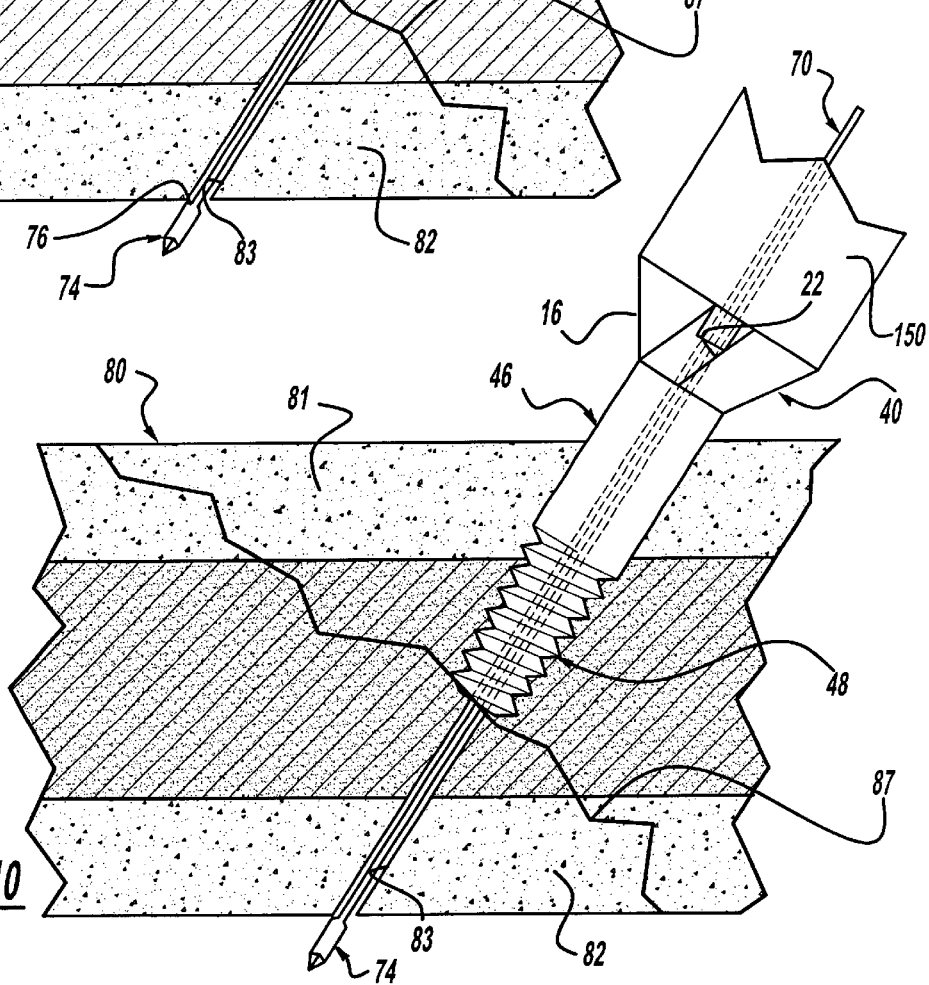
FIG. 10 is a partial side sectional view of a fastener according to the invention partially driven in the bone material.
Figure 11:
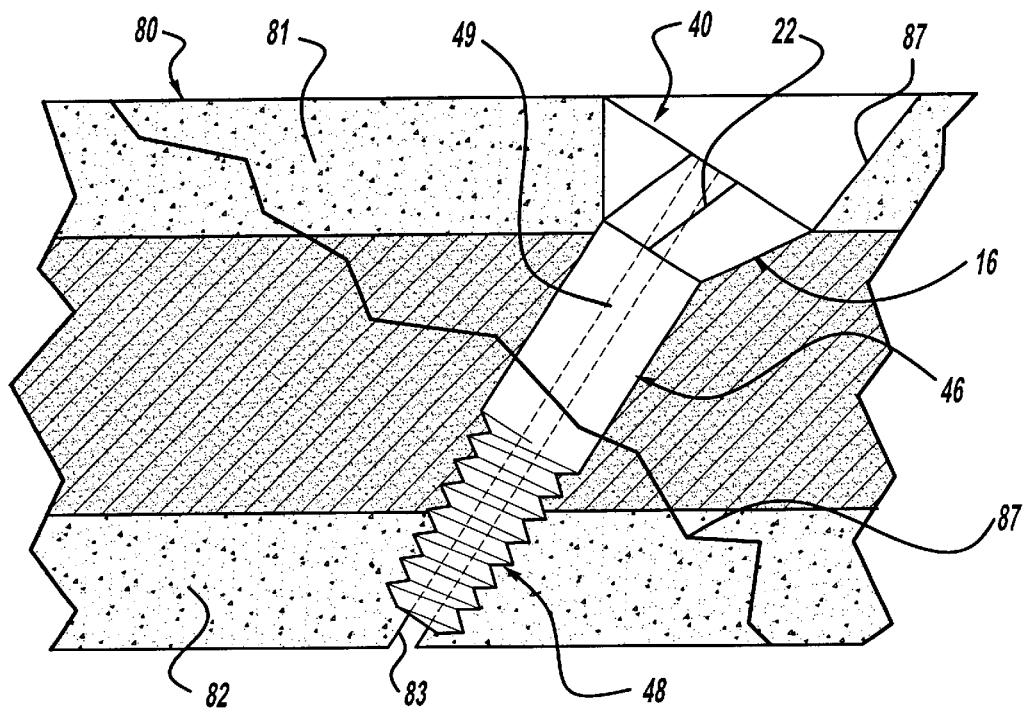
FIG. 11 is a partial side sectional view of the fastener of FIG. 10 fully driven in the bone material.

As shown in FIG. 10, after the guide wire 70 is used to initially penetrate the fractured bone, particularly driving through an undulated fracture 87, the threaded fastener 40 is slid axially over the wire 70, which guides the threaded fastener 40 during insertion in the bone material 80. A driver drives the threaded fastener 40 into the bone material 80, guided by the guide wire 70. As shown in FIG. 11, the top of the head portion 16 is fully inserted into the bone material 80 and properly seated flush or nearly flush with the near side bone cortex 81. Once the fastener 40 is fully inserted into the bone material 80 so that the head portion 16 is flush, the guide wire 70, which serves as a guide for the threaded fastener 40 during insertion thereof into the bone material 80, is removed by withdrawal through the through-passage 49 of the fastener 40, thus completing the repair.

Preferably, the driver 150 is used to insert the fastener 40 by applying torque along the peripheral edge of the fastener head 16, as shown in FIG. 10. The fastener 40 is inserted until, as shown in FIG. 11, the threaded fastener 40 forms its own countersunk recess 87. More particularly, the cutting edges 22 burr the bone material of the near-side cortex 81 until the head portion 16 of the threaded fastener 40 is embedded therein. The burred bone material passes through the arcuate grooves 23 as the fastener 40 is inserted, thereby easing resistance to insertion of the fastener 40. Where the driver 150' is used to drive the fastener 40, the reliefs 160 of the prongs 156' further accommodate the flow of burred bone material during insertion. Further, even when the driver 150 is used to insert the fastener 40, the prongs 156, while occupying more of the fastener head grooves 23 and thereby narrowing the flow path, do not block the flow of bone material. Finally, a conventional driver can be used to insert the fastener 40 by including the appropriate slot, phillips, or hex-socket head on the fastener 40.

Figure 12:
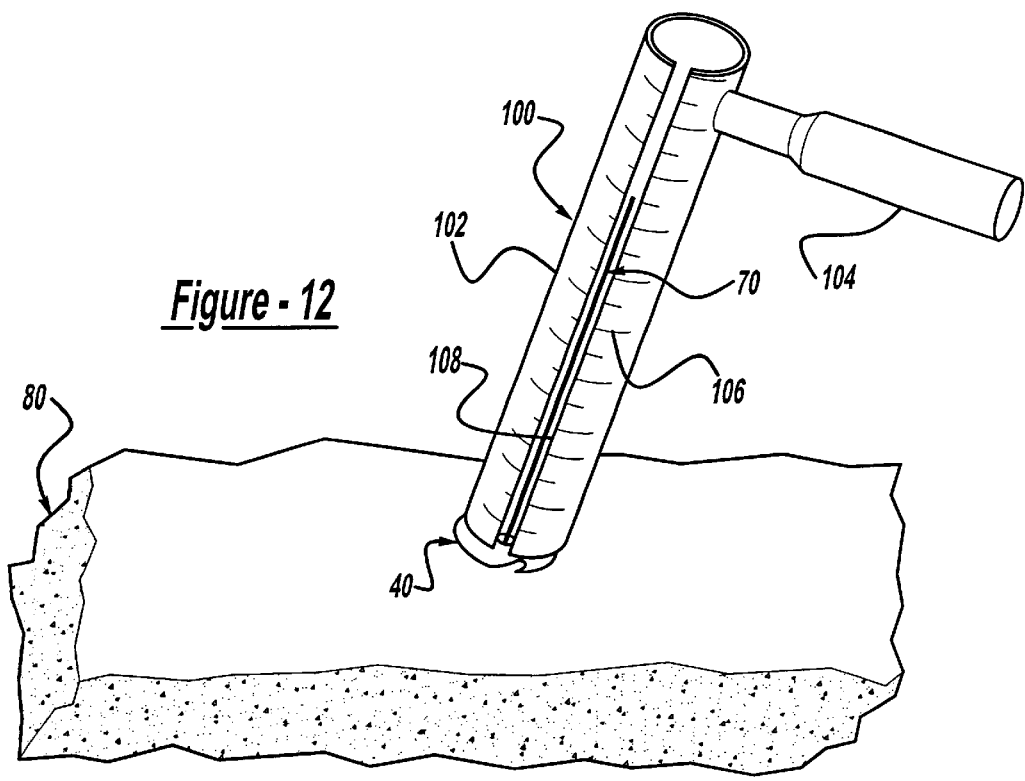
FIG. 12 is a partial perspective view of an alternative embodiment of a measuring device.
Figure 13:
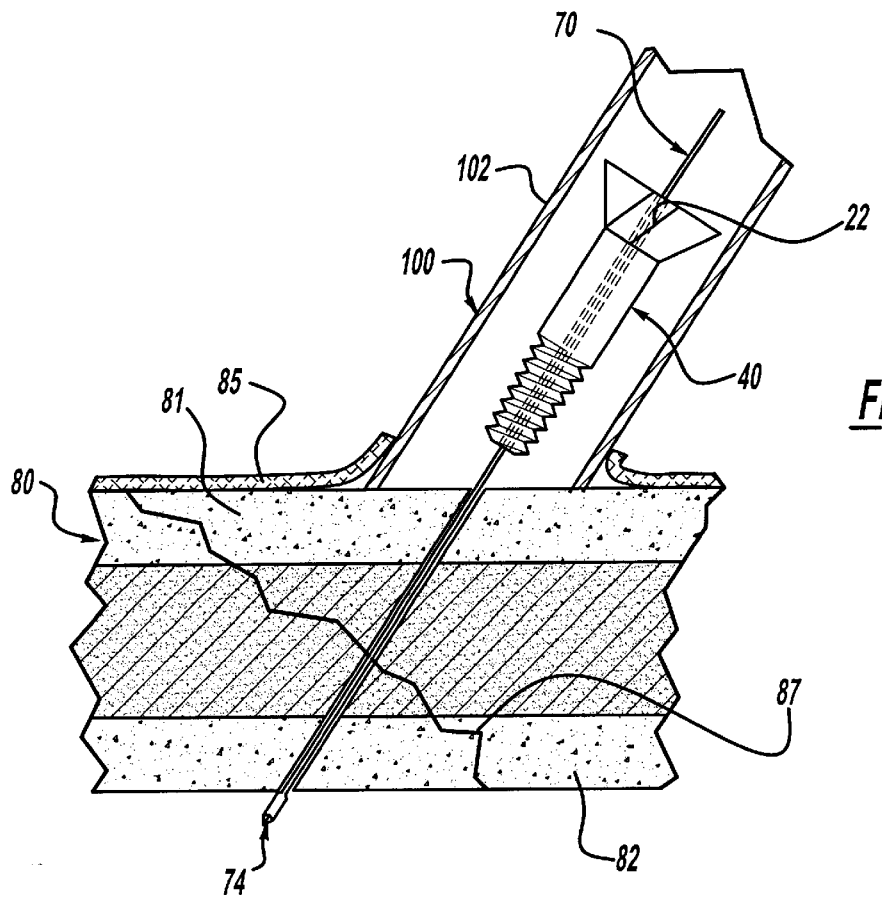
FIG. 13 is a partial side sectional view of a fastener being guided by a guide wire disposed within the measuring device of FIG. 12 prior to being driven in the bone material.
Figure 14:
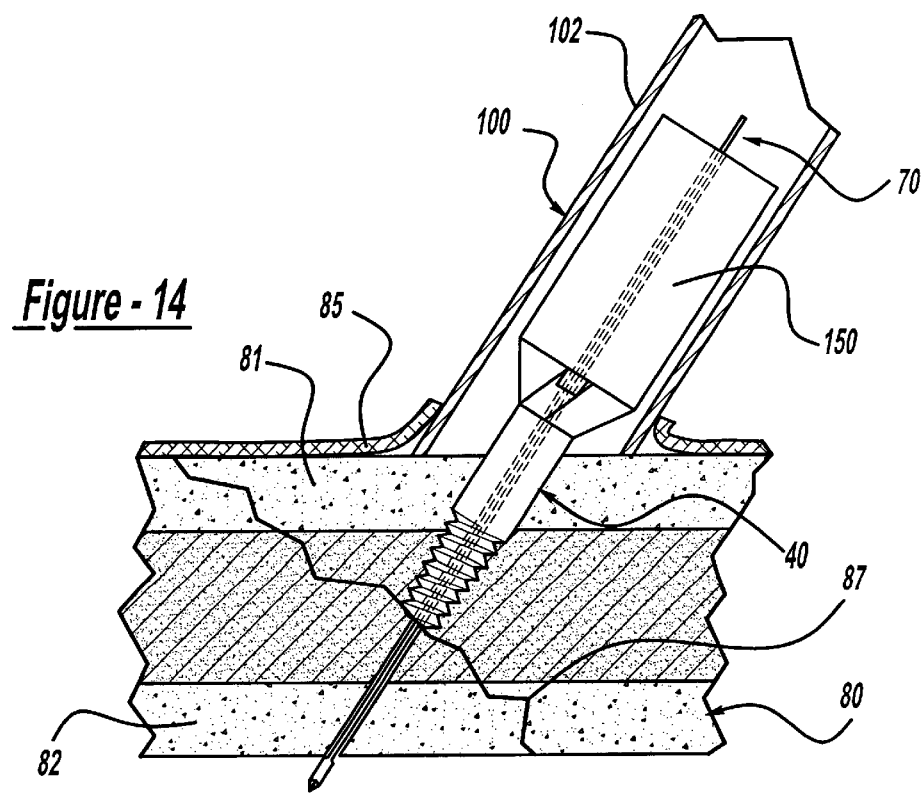
FIG. 14 is a partial side sectional view of the fastener of FIG. 13 partially driven in the bone material by a driver according to the invention.
Figure 15:
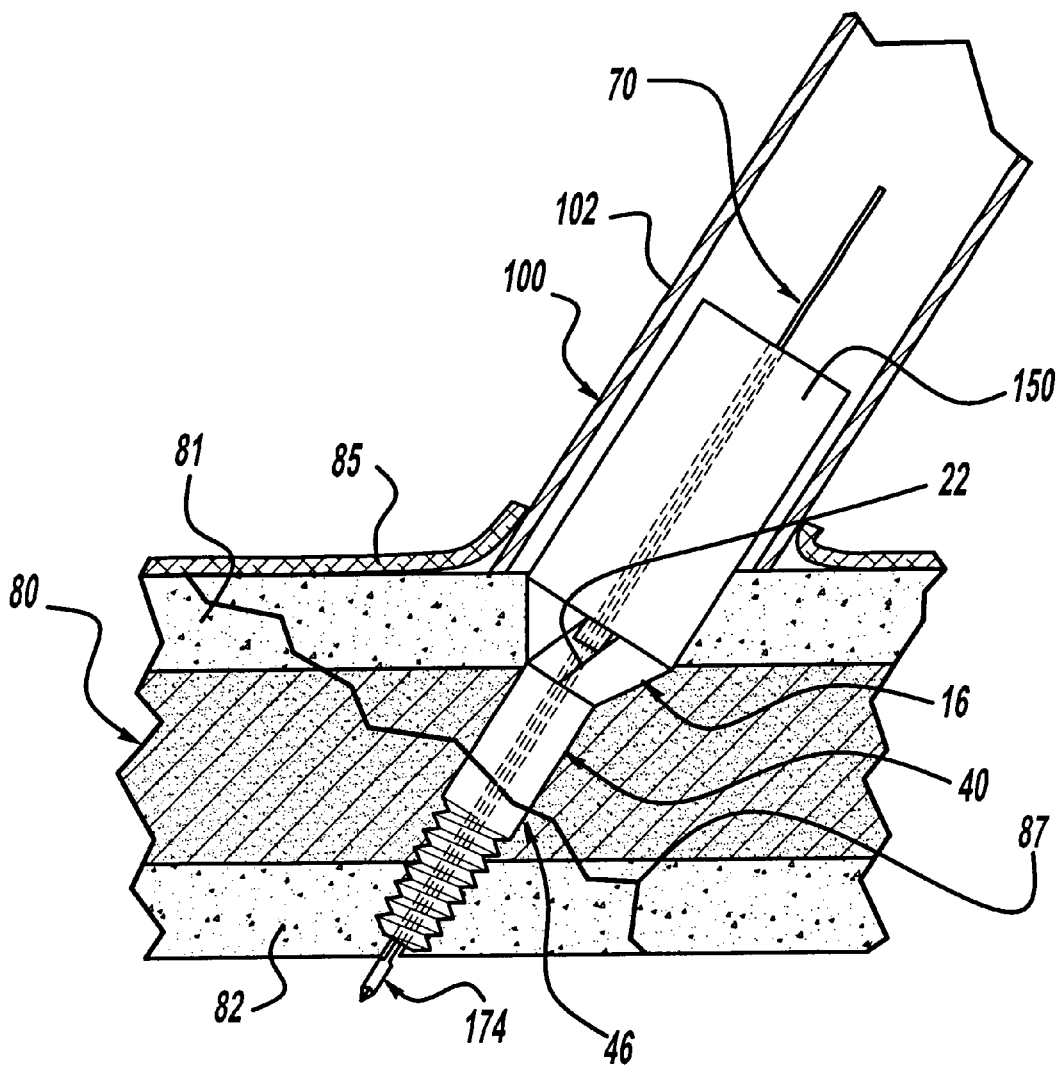
FIG. 15 is a partial side sectional view of the fastener of FIG. 14 fully inserted in the bone material by the driver.

An alternative embodiment of the invention including a measuring device 100 having a cylindrical body 102 and a handle 104 disposed generally perpendicular to the longitudinal axis of the body 102 is shown in FIG. 12. The cylindrical body 102 includes a graduated scale 106 along an axial slot 108 formed in the cylindrical body 102 to facilitate measurement of the depth of the bore 83 through the bone material 80. Further, the measuring sleeve 100 serves to protect soft tissue from the fastener head 16 and threads 49 during insertion of the fastener 40 into the bone material 80. Moreover, the measuring sleeve 100 facilitates closed or minimal incision conditions, which further simplify and quicken bone repair procedures. Finally, the measuring sleeve 100 is particularly useful for questionable or non-sterile surroundings or for veterinary use.

In use, the measuring device 100 is lowered over the guide wire 70 and through comparison of the length of the guide wire 70, or a mark on the guide wire 70, as visible through the slot 108, to the calculated values on the body 102 of the measuring device 100, the desired fastener 40 length can be determined visually. Preferably, the body 102 includes at least two different sets of measurement values, one corresponding to a technique where the end of the guide wire 70 exits the far side bone cortex 82 and the other corresponding to a technique where the end of the guide wire 70 does not exit the far side bone cortex 82.

Also, the measuring device 100 allows the fastener 40 to be utilized under closed or minimal incision conditions, which will further simplify and quicken fixation procedures. For example, the guide wire 70 can fixate the fracture or osteotomy percutaneously (or through the skin without opening the site and fully exposing the bone). Then, via a small stab incision on either side of the guide wire 70, the soft tissue 85 can be bluntly dissected down to the surface of the bone 81 and the measuring device slid over the guide wire 70 until it stops at the bone surface 81. Then, fixation via the threaded fastener 40 is accomplished in the same manner as if the surgical site was open. The measuring device 100 further functions as a soft tissue protector from the threads 49 of the fastener 40 during fixation.

Overall, the cannulated fastener assembly for repairing a bone fracture including the threaded fastener 40, guide wire 70, measuring sleeve 100, and driver 150, 150' maximizes simplicity and cost effectiveness. The fastener 40 provides an improved structure at a reasonable cost for self-tapping, self-drilling, and self-countersinking in a bone to be repaired. Further, the guide wire 70 eases insertion of the fastener 40 and simplifies measurement of a bore in bone material, whereby the depth of a fractured bone to be repaired can be easily determined so that an appropriately sized fastener can be selected to repair the fracture. The driver 150 efficiently drives the fastener 40 by applying torque at the periphery of the fastener head 16.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A fastener assembly for repairing fractured bone material, comprising:
   a wire including a wire leading end for forming a bore through the bone material and a wire trailing end for extending beyond a near-side cortex of the bone material; and
   a fastener including a head portion having at least one head cutting edge, a lower portion having threads, and an axial aperture therethrough for receiving said wire, said fastener adapted to slide axially over said wire trailing end and be driven toward said wire leading end to countersink in the bone material.

2. The fastener assembly according to claim 1 wherein said at least one head cutting edge is multiple spaced-apart head cutting edges.

3. The fastener assembly according to claim 2 wherein said head cutting edges are preferably angled between 15 and 30 degrees relative a longitudinal axis of said fastener.

4. The fastener assembly according to claim 1 wherein said threads are self-tapping.

5. The fastener assembly according to claim 1 wherein said lower portion includes first cutting edges at a lower end thereof, said first cutting edges being adapted to cut through the bone material during insertion of said fastener.

6. The fastener assembly according to claim 5 wherein said first cutting edges are fluted.

7. The fastener assembly according to claim 5 wherein said lower portion includes second cutting edges at an upper end thereof, said second cutting edges being adapted to cut through the bone material during removal of said fastener.

8. The fastener assembly according to claim 1 wherein said lower portion includes elongated cutting edges extending from a lower end to an upper end thereof, said elongated cutting edges being adapted to cut through the bone material during insertion and removal of said fastener.

9. The fastener assembly according to claim 8 wherein said elongated cutting edges are fluted.

10. The fastener assembly according to claim 1 wherein said wire includes a cutting tip for boring through the bone material.

11. The fastener assembly according to claim 1 wherein said wire leading end is adapted to pierce a far-side cortex of the bone material.

12. The fastener assembly according to claim 11 further comprising a measuring device for determining the length of the bore through the bone material.

13. The fastener assembly according to claim 12 wherein the measuring device is a ruler having graduations thereon and adapted to be positioned generally parallel to said wire trailing end and abutting the near-side cortex of the bone material.

14. The fastener assembly according to claim 13 wherein the measuring device is a measuring sleeve including a tubular body having graduations thereon and adapted to be positioned generally coaxially relative said wire trailing end and abutting the near-side cortex of the bone material.

15. A fastener for repairing fractured bone material, comprising:
   an elongated body including a threaded portion and a guide aperture therethrough, said threaded portion including threads, said guide aperture being adapted to axially receive a guide wire for guiding said fastener through the bone material; and
   a head portion at one end of said elongated body, said head portion including at least one head cutting edge, whereby the fastener is adapted to countersink in the bone material.

16. The fastener assembly according to claim 15 wherein said at least one head cutting edge is preferably angled between 15 and 30 degrees relative a longitudinal axis thereof.

17. The fastener assembly according to claim 15 wherein said threads are self-tapping.

18. The fastener assembly according to claim 15 wherein said threaded portion further includes at least one body cutting edge for cutting through the bone material.

19. The fastener assembly according to claim 18 wherein said at least one body cutting edge includes a first cutting edge disposed at a lower end of said threaded lower portion, said first cutting edge being adapted to cut through the bone material during insertion of said fastener.

20. The fastener assembly according to claim 19 wherein said first cutting edge is fluted.

21. The fastener assembly according to claim 19 wherein said at least one body cutting edge further includes a second cutting edge at an upper end of said threaded lower portion, said second cutting edge being adapted to cut through the bone material during removal of said fastener.

22. The fastener assembly according to claim 21 wherein said second cutting edge is fluted.

23. The fastener assembly according to claim 18 wherein said at least one body cutting edge extends from a lower end to an upper end of said threaded lower portion, said at least one body cutting edge being adapted to cut through the bone material during insertion and removal of said fastener.

24. The fastener assembly according to claim 23 wherein said at least one body cutting edge is fluted.

25. A fastener system for repairing fractured bone material, comprising:
   a guide wire including a wire leading end for forming a bore through the bone material and a wire trailing end for extending beyond a near-side cortex of the bone material;
   a fastener including an elongated body having a fastener head portion and a threaded lower portion, said elongated body including an axial aperture therethrough for accommodating said guide wire, said fastener head portion including spaced-apart cutting edges for countersinking said fastener in the bone material; and
   a driver including a driver body and driver head, said driver body including an axially disposed aperture therethrough for accommodating said guide wire, said driver head including fingers adapted to engage said spaced-apart cutting edges of said fastener head portion for driving said fastener in the bone material.

26. The fastener assembly according to claim 25 wherein said spaced-apart cutting edges are preferably angled between 15 and 30 degrees relative a longitudinal axis of said fastener.

27. The fastener assembly according to claim 25 wherein said threaded lower portion includes self-tapping threads.

28. The fastener assembly according to claim 25 wherein said threaded lower portion includes at least one body cutting edge.

29. The fastener assembly according to claim 28 wherein said at least one cutting edge includes a first cutting edge disposed at a lower end of said threaded lower portion, said first cutting edge being adapted to cut through the bone material during insertion of said fastener.

30. The fastener assembly according to claim 29 wherein said first cutting edge is fluted.

31. The fastener assembly according to claim 29 wherein said at least one body cutting edge further includes a second cutting edge at an upper end of said threaded lower portion, said second cutting edge being adapted to cut through the bone material during removal of said fastener.

32. The fastener assembly according to claim 30 wherein said second cutting edge is fluted.

33. The fastener assembly according to claim 28 wherein said at least one body cutting edge extends from a lower end to an upper end of said threaded lower portion, said at least one body cutting edge being adapted to cut through the bone material during insertion and removal of said fastener.

34. The fastener assembly according to claim 33 wherein said at least one body cutting edge is fluted.

35. A method for repairing fractured bone material, comprising:

forming a bore through the bone material with a guide wire, said guide wire including a trailing end for extending beyond a near-side cortex of the bone material;

coaxially disposing a cannulated fastener over said trailing end of said guide wire;

driving said fastener along said guide wire and through the bone material; and countersinking said fastener head in the bone material.

36. The method according to claim 35 further comprising measuring the length of said wire trailing end extending beyond the near-side cortex of the bone material, whereby the length of said fastener can be selected.

37. The method according to claim 36 wherein said step of measuring includes coaxially disposing a measuring sleeve about said wire trailing end extending beyond the near-side cortex of the bone material, said measuring sleeve including a graduated scale for determining the depth of the bore through the bone material.

38. The method according to claim 35 wherein the step of driving the fastener includes driving the fastener with a driver including prongs adapted to engage spaced-apart openings in a head of said fastener for driving said fastener in the bone material.

\* \* \* \* \*